United States Patent
Zhang et al.

(10) Patent No.: US 7,655,596 B2
(45) Date of Patent: Feb. 2, 2010

(54) CATALYST FOR EPOXIDATION OF AN ALKENE TO AN ALKENE OXIDE, METHOD OF MAKING AND METHOD OF USING THEREOF

(75) Inventors: Xiankuan Zhang, Houston, TX (US); Alla Konstantin Khanmamedova, Sugar Land, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 540 days.

(21) Appl. No.: 11/316,031

(22) Filed: Dec. 22, 2005

(65) Prior Publication Data

US 2007/0149792 A1 Jun. 28, 2007

(51) Int. Cl.
*B01J 23/48* (2006.01)

(52) U.S. Cl. .................. 502/348; 502/231; 502/340; 502/347; 502/344; 502/341; 549/535; 549/536; 549/534

(58) Field of Classification Search .................. None
See application file for complete search history.

(56) References Cited

U.S. PATENT DOCUMENTS

| | | | |
|---|---|---|---|
| 4,829,044 A | 5/1989 | Boxhoorn et al. | |
| 4,874,739 A | 10/1989 | Boxhoorn | |
| 4,939,114 A | 7/1990 | Nojiri et al. | |
| 5,102,848 A | 4/1992 | Soo et al. | |
| 5,187,140 A | 2/1993 | Thorsteinson et al. | |
| 5,733,842 A * | 3/1998 | Gerdes et al. | 502/439 |
| 6,579,825 B2 | 6/2003 | Lockemeyer | |
| 6,656,874 B2 | 12/2003 | Lockemeyer | |
| 2005/0027133 A1 * | 2/2005 | Hooks et al. | 549/535 |

OTHER PUBLICATIONS

"Solid State Chemistry and Its Appications"; Anthony R. West; p. 292-296; John Wiley & Sons (1984).

* cited by examiner

*Primary Examiner*—Melvin C Mayes
*Assistant Examiner*—Smita Patel
(74) *Attorney, Agent, or Firm*—Jim Wheelington

(57) ABSTRACT

The present invention if for a catalyst for epoxidation of an alkene, such as ethylene, to an alkene oxide, such as ethylene oxide, on which silver has been deposited on alumina as a support which has been modified with certain weak base compounds, such as oxides of a Group 1A, Group 2A, Group 3A or the first transition series of the Periodic Table of Elements, and with a high temperature heat treatment. Optional promoters selected from the group consisting of compounds of Group 1A, Group 2A, Group 7A and Group 8 may be contacted with the alpha-alumina support in solution with a silver compound, with the catalyst precursor before calcination or with the catalyst after calcination. The catalyst is brought into contact with alkene and oxygen under reaction conditions to selectively convert the alkene to an alkene oxide.

13 Claims, No Drawings

CATALYST FOR EPOXIDATION OF AN ALKENE TO AN ALKENE OXIDE, METHOD OF MAKING AND METHOD OF USING THEREOF

BACKGROUND OF THE INVENTION

1. Field of the Invention

This invention relates to a catalyst for epoxidation of an alkene, such as ethylene, to an alkene oxide, such as ethylene oxide. Specifically, this invention relates to a catalyst on which silver has been deposited on alumina as a support which has been modified with certain weak base compounds, such as oxides of a Group 1A, Group 2A, Group 3A or the first transition series of the Periodic Table of Elements, and with a high temperature heat treatment or calcination.

2. Description of the Prior Art

The production of alkene oxides from alkenes is known and is practiced commercially. Of particular interest is the production of ethylene oxide from ethylene with a catalyst of a refractory material, such as alpha-alumina, on which silver has been deposited. Other materials may also be deposited on the support to promote the reaction.

U.S. Pat. No. 4,939,114 discloses production of ethylene oxide by oxidation of ethylene with a catalyst on which silver and at least one cationic component selected from sodium, potassium, rubidium and cesium have been deposited on an alpha-alumina which does not show acidity and basicity within a particular pKa range tested by color change. The impregnated carrier is heat treated for 5-30 minutes with air at 130-300° C.

U.S. Pat. No. 5,187,140 epoxidation of ethylene to ethylene oxide with catalyst having a high silver content on carriers having a high surface area and a high pore volume. The surface acidity of the carrier is less than about 2, preferably less than about 1.5 and often between 0.05 to 1.0 micromoles per gram of carrier. The impregnated carrier is heated to reduce the silver compound to metallic silver at a temperature of 100-900° C.

U.S. Pat. No. 5,102,848 discloses epoxidation of ethylene with a catalyst of a silver-impregnated support which has an essential absence of fluoride anion but may have a fluoride anion present in an amount sufficient to reduce ethylene oxide burning. The surface acidity of the carrier is less than about 2, preferably less than about 1.5 and often between 0.05 to 1.0 micromoles per gram of carrier. The impregnated carrier was calcined at 500° C. for 2.5 minutes in Examples 1-7 and at 500° C. for 3 minutes in Examples 8 and 9.

U.S. Pat. No. 4,829,044 discloses a process for the preparation of a silver-containing catalyst for the oxidation of ethylene to ethylene oxide by impregnating a calcined alkali metal enriched alumina carrier with a silver compound and a potassium, rubidium or cesium compound as a promoter.

U.S. Pat. No. 4,874,739 discloses a process for the preparation of a silver-containing catalyst for the oxidation of ethylene to ethylene oxide by mixing alumina with a tin compound and an alkali metal compound, calcining the modified alumina, impregnating the carrier with a silver compound and with an alkali metal compound and a rhenium compound as promoters. The alkali metal promoter may serve to neutralize "acid sites" on the alumina surface to influence formation of carbon dioxide from ethylene oxide.

U.S. Pat. No. 6,656,874 discloses a process for depositing metals, such as silver, on a carrier by impregnation with a solution which has pH lowered to above 11.2. Since the typical impregnation solution for an epoxidation catalyst is quite basic, a strong base is used to farther lower the pH. Examples of strong bases include alkylammonium-hydroxides, such as tetraethylammonium hydroxide, and metal hydroxides, such as lithium hydroxide and cesium hydroxide. While lowering the concentration of ionizable species on the surface of the carrier prior to deposition may improve performance, use of aggressive media, such as acid or bases, is not recommended since they extract material and generate acidic or basic sites in the pores.

U.S. Pat. No. 6,579,825 discloses a catalyst carrier of a refractory inorganic material on which the concentration of ionizable species has been lowered, particularly such that the carrier has a sodium solubilization rate no greater than 5 ppmw/5 minutes. Acids will remove cations on a carrier but are fairly ineffectual in removing anions, such as silicates.

It would be advantageous to modify the alpha-alumina support without depending on production control of the raw materials in making alpha-alumina and to modify not only the surface of the alpha-alumina but also the bulk properties at least in part.

SUMMARY OF THE INVENTION

The invention provides a catalyst for producing ethylene oxide from ethylene and oxygen, a method of making the catalyst and a method of using the catalyst. The catalyst comprises a) a support of alpha-alumina;

b) a catalytically effective amount of silver; and c) optionally, promoters selected from the group consisting of compounds of Group 1A, Group 2A, Group 7A and Group 8.

The support is an alpha-alumina which has been modified with certain weak base compounds, such as oxides of a Group 1A, Group 2A, Group 3A or the first transition series of the Periodic Table of Elements, and with a high temperature heat treatment or calcination.

The alpha-alumina support may be contacted with a solution containing a silver compound and, optionally, compounds of the promoters and the catalyst is then calcined. Alternatively, the compounds of the promoters can be contacted with the catalyst precursor before calcination or the catalyst after calcination. The catalyst may be formed into shapes suitable for a reactor in which to selectively convert ethylene to ethylene oxide.

The catalyst is brought into contact with alkene and oxygen under reaction conditions to selectively convert the alkene to an alkene oxide.

DETAILED DESCRIPTION OF THE INVENTION

The present invention is for a silver-containing catalyst, a method of preparing such a catalyst and a method of using such a catalyst in a process of making an alkene oxide from an alkene and an oxygen-containing gas by oxidation of the alkene to the corresponding epoxide. The catalytically active silver is supported on an alpha-alumina.

In this Specification, including the Claims, certain terms are used with the following meaning and definitions.

The term "support" refers to a carrier on which the catalytically active components, e.g., silver and optional promoters, of the catalyst are deposited.

The term "promoter" refers to a component of a catalyst that provides improvement in one or more of the properties of the catalyst, e.g., selectivity, activity, conversion, stability and yield as compared to a catalyst not containing the promoter.

The term "modifier" refers to a weak base compound that is used to treat the support prior to contacting the support with the catalytically active components of the catalyst.

In general, the catalyst is prepared by forming a solution of a silver compound and optional promoter compounds, contacting the solution with the support and reducing the silver compound to elemental silver. The silver compound can be an oxide, a salt or carboxylate. Examples of the silver compound are silver oxide, silver nitrate, silver carbonate, silver acetate, silver propionate, silver butyrate, silver oxalate, silver malonate, silver malate, silver maleate, silver lactate, silver citrate, and silver phthalate. The silver concentration in the finished catalyst is at least a catalytically effective amount, preferably from about 2-50 percent by weight, more preferably from about 5-30 percent by weight, most preferably from about 8-15 percent by weight.

Optional promoters compounds, such as compounds of alkali metals, other metals or halides, may be added to the solution or may be added to the solid catalyst after reduction. Examples of alkali metal promoters are compounds of sodium, potassium, rubidium and cesium, such as cesium hydroxide, cesium chloride and cesium nitrate. The promoter compounds can be added as salts, preferably carbonates, nitrates or nitrites.

Any of these promoters may be added with the silver compound in solution, to the solid catalyst precursor before calcination or to the calcined catalyst. The promoters are present in the catalyst in the amount of from about 20-5000 ppm, preferably 50-2000 ppm, most preferably 100-1000 ppm.

The support of this invention is alpha-alumina or aluminum oxide, $Al_2O_3$, which has a melting point of about 2,000° C. and a specific gravity of about 4.0. It is insoluble in water and organic liquids and very slightly soluble in strong acids and bases. Alumina occurs in two crystalline forms: alpha-alumina composed of colorless hexagonal crystals with the properties given above and gamma-alumina composed of minute colorless cubic crystals with specific gravity of about 3.6 that are transformed to the alpha form at high temperatures. The composition of the alpha-alumina is a $A_2O_3$ content of greater than 90%, a $SiO_2$ content of less than 10% and an other oxides, such as $Na_2O$ and $CaO$, content of less than 0.05% for each compound.

In the present invention, the alpha-alumina support is modified with certain weak base compounds and with a high temperature heat treatment or calcination. The support is contacted is with a weak base compound using the incipient wetness technique.

The weak base compound of the present invention can be characterized by the partial charge of the compound. Atoms of high electronegativity attract electron and acquire a partial negative charge. When atoms combine chemically to form a compound, the electronegativity of the compound is of some intermediate sum which can be calculated and expressed as a "partial charge" to characterize the compound. [see "Solid State Chemistry and its Applications", Anthony R. West, p. 292-296, John Wiley & Sone (1984)]. The acidic amphoteric and basic properties of oxides correlate with the partial charge. A partial charge of less than about −0.3 is considered a solid compound with basic properties. A weak base compound of the present invention has a partial charge of from about −0.3 to about −0.95. Examples of the weak base compound are oxides of a Group 1A, Group 2A, Group 3A (IUPAC designation) or the first transition series of the Periodic Table of Elements. The weak base compound may be a single metal oxide, such a calcium oxide (CaO), or may contain additional elements that do not change the weak base character of the compound. Examples of these additional elements are aluminum, silicon, phosphorus, gallium, germanium and arsenic, especially aluminum and silicon.

After contact with the weak base compound, the alpha-alumina is heat treated or calcined. The temperature of this first calcination ("support calcination") is in the range from 500 to 900° C. for 5 to 50 hours.

The alpha-alumina may be dried before calcination. The drying may occur by heating the alpha-alumina from room temperature to the calcination temperature. The temperature ramp of the drying can be at a ramp from 1° C. to 15° C. per minute, preferably about 10° C. per minute.

Without being limited by theory, it is believed that modification of the alpha-alumina with a weak base and with high temperature heat treatment or calcination affects the composition, content and properties of the alpha-alumina. The extent of the modification is believed to extend not only to the surface but also to a depth of several monolayers. With a monolayer being 1.5-2 angstroms, the modification may reach a depth of one to twenty monolayers. The modified support will contain an amount of the weak base compound in the range from 20 to 10,000 ppm, preferably 50 to 1000 ppm.

The solution of the silver compound and optional promoter compounds is contacted with the modified support by incipient wetness technique to form a catalyst precursor. The catalyst precursor must be calcined to reduce the silver compound to elemental silver to have an effective catalyst for epoxidation of an alkene to an alkene oxide. This second calcination ("catalyst calcination") may also further dry the catalyst precursor and support, react the non-silver components and remove volatile compounds. The temperature of the catalyst calcination should be at a temperature of from about 200-400° C., preferably 220-350° C., more preferably 250-300° C. for a time of from about 2-30 minutes, preferably 10-20 minutes, more preferably about 20 minutes. The catalyst calcination may be in one stage or multiple stages. Without the present invention and its claims being limited by theory, it believed that exposing the catalyst precursor to these elevated temperatures reduces the silver to its elemental form but that while other components (alkali earth metal carbonate, alkali metals, other metals or halides) may react during calcination they are not reduced to their elemental form.

The catalyst precursor may be dried before catalyst calcination. The drying may occur by is heating the catalyst precursor from room temperature to the calcination temperature. The temperature ramp of the drying can be at a ramp from 1° C. to 15° C. per minute, preferably about 10° C. per minute.

The catalyst is brought into contact with an alkene, such as ethylene, and oxygen under reaction conditions to selectively convert the alkene to an alkylene oxide. Typical conditions for the epoxidation reaction are temperatures from 170-300° C., preferably 200-280° C., and pressures from about 100-500 psig, preferably about 200-400 psig. The alkene is present in the amount from about 1-50% by volume, preferably 10-40% by volume, more preferably from about 20-30% by volume. Oxygen is present in amount from about 3-20% by volume, preferably 5-15% by volume, more preferably about 8-12% by volume. The feedstream may optionally contain other gaseous species, such as organic halides, e.g., ethylene dichloride (EDC), present in the feedstream in the amount of from 0.2-25 ppm.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLES

CaO: Source: Ca(NO$_3$)$_2$, 900° C., 5 hrs

Example 1

Preparation of modified support: 28.4 g support rings (Norpro SA5552) was impregnated with 7.7 ml of an aqueous solution of 1.24 wt % Ca(NO$_3$)$_2$ [Ca(NO$_3$)$_2$.4H$_2$O, Aldrich, 99.99%] in a round flask. The impregnated support with residual solution was rotary evaporated under vacuum for 5-7 minutes or till no residual solution is visible. During the rotary evaporation, the flask was exposed to atmosphere for 2-3 times to ensure uniform distribution of the solution throughout the support. The impregnated support was then dried and calcined in a muffle furnace in air at 120° C. for 10 minutes and 900° C. for 5 hours before naturally cooled to ambient temperature. This will result in a support containing 1000 ppm CaO.

Preparation of catalyst: 4 ml an aqueous solution of 0.17 wt % CsCl (Aldrich 99.9%) and 1 ml DI water were placed inside a tinted beaker and the beaker was placed in an ice bath. 2.7 ml ethylenediamine (EN) (Alfa, 99+%) was added gradually with the solution being stirred with a magnetic stirrer. 5.7 g silver oxalate prepared in-house was introduced and dissolved into the water-EN solution in small portions. Temperature was maintained below 20° C. during preparation of the silver-amine solution. 25.9 g modified support rings were placed into a 100 ml round bottom flask and evacuated for 5-7 minutes. The silver-amine solution was poured onto the rings. After shaking to distribute the solution uniformly over the rings, the impregnated rings were rotary evaporated under vacuum for 5-7 minutes. During the rotary evaporation, the flask was exposed to atmosphere for 2-3 times. The impregnated support rings were placed into a calcination dish. The calcination was performed in a muffle furnace in air at 260° C. for 10 minutes and then 250° C. for 10 minutes before being allowed to cool to ambient temperature with the furnace door being slightly open. This will result in a catalyst containing 13.5% Ag and 180 ppm Cs. The catalyst in ring shape was crushed and sieved to 40 mesh and ready for testing.

Testing of catalyst: 2 ml catalyst was charged into a ¼" stainless steel U-tube reactor, and the catalyst bed height was about 5". Quartz wool was used at the bottom and top of the catalyst to support the catalyst and also prevent the catalyst from being blown away. The U-tube with the catalyst was placed in a sand bath and connected to feed supply and product exit lines. A K-type thermocouple was attached to the U-tube to monitored temperature. After passing leak check, the sand bath was heated to 220° C. under a flowing feed mixture of 25% C$_2$H$_4$, 10% O$_2$, 10% CO$_2$, 1 ppm EDC, and balance CH$_4$ at a total GHSV of 5000 h$^{-1}$ at a total pressure of 300 psig. The reaction temperature was adjusted to obtain the target conversion of about 10%. Feed and product analysis was performed by an online GC. Methane, a balance gas, was used as an internal standard for calculating conversion and selectivity. Carbon mass balance was typically within ±3%. After about 24 hours on stream, the catalyst gave 10.1% ethylene conversion and 82.4% selectivity to ethylene oxide at 223° C.

Example 2

The catalyst was synthesized and tested as described in Example 1, except the amount of Ca(NO$_3$)$_2$ was altered so that the support was modified with 500 ppm CaO. Ethylene conversion was 10.2% and EO selectivity was 82.7% at 222° C.

Example 3

The catalyst was synthesized and tested as described in Example 1, except the amount of Ca(NO$_3$)$_2$ was altered so that the support was modified with 50 ppm CaO. Ethylene conversion was 10.3% and EO selectivity was 83.2% at 227° C.

TABLE 1

| Example | CaO ppm | T ° C. | Ethylene Conv. % | EO Sel. % | EO Yield % |
|---|---|---|---|---|---|
| 1 | 1000 | 223 | 10.1 | 82.4 | 8.3 |
| 2 | 500 | 222 | 10.2 | 82.7 | 8.4 |
| 3 | 50 | 227 | 10.3 | 83.2 | 8.6 |

Source: Ca(OH)$_2$, 900° C., 5 hrs

Example 4

26.8 g support rings (Norpro SA5552) was impregnated with 7.2 ml of an aqueous solution of 1.24 wt % Ca(NO$_3$)$_2$ [Ca(NO$_3$)$_2$.4H$_2$O, Aldrich, 99.99%] in a round flask. The impregnated support with residual solution was rotary evaporated under vacuum for 10 minutes or till no residual solution is visible. During the rotary evaporation, the flask was exposed to atmosphere for 2-3 times to ensure uniform distribution of the solution throughout the support. The support was then dried at 120° C. for 10 hours. The same procedure was followed to impregnate 7.2 ml of an ammonia solution (28-30 wt % NH$_4$OH, Sigma-Aldrich). After the second impregnation, the support was dried and calcined in a muffle furnace in air at 120° C. for 10 hours, and 900° C. for 5 hours. This will result in a support containing 1000 ppm CaO.

The catalyst was synthesized and tested as described in Example 1. Ethylene conversion was 10.4% and EO selectivity was 80.0% at 223° C.

Example 5

The catalyst was synthesized and tested as described in Example 4, except the amount of Ca(NO$_3$)$_2$ was altered so that the support was modified with 500 ppm CaO. Ethylene conversion was 10.2% and EO selectivity was 81.7% at 224° C.

Example 6

The catalyst was synthesized and tested as described in Example 4, except the amount of Ca(NO$_3$)$_2$ was altered so that the support was modified with 100 ppm CaO. Ethylene conversion was 10.9% and EO selectivity was 81.9% at 225° C.

Example 7

The catalyst was synthesized and tested as described in Example 4, except the amount of Ca(NO$_3$)$_2$ was altered so that the support was modified with 50 ppm CaO. Ethylene conversion was 10.0% and EO selectivity was 81.8% at 226° C.

TABLE 2

| Example | CaO ppm | T ° C. | Ethylene Conv. % | EO Sel. % | EO Yield % |
|---|---|---|---|---|---|
| 4 | 1000 | 223 | 10.4 | 80.0 | 8.3 |
| 5 | 500 | 224 | 10.2 | 81.7 | 8.3 |
| 6 | 100 | 225 | 10.9 | 81.9 | 8.9 |
| 7 | 50 | 226 | 10.0 | 81.8 | 8.2 |

CaO: Source: Calcium lactate, 500° C., 47 hrs

Example 8

25.9 g support rings (Norpro SA5552) was impregnated with 7.0 ml an aqueous solution of 1.64 wt % Ca[CH₃CH(OH)CO₂]₂ (Calcium Lactate.5H₂O, Aldrich, 99.99%) in a round flask. The impregnated support with residual solution was rotary evaporated under vacuum for 10 minutes or till no residual solution is visible. During the rotary evaporation, the flask was exposed to atmosphere for 2-3 times to ensure uniform distribution of the solution throughout the support. The support was calcined in a muffle furnace in air at 120° C. for 15 hours and 500° C. for 47 hours. This will result in a support containing 1000 ppm CaO.

The catalyst was synthesized and tested as described in Example 1. Ethylene conversion was 10.1% and EO selectivity was 78.7% at 214° C.

Example 9

The catalyst was synthesized and tested as described in Example 8, except the amount of Ca[CH₃CH(OH)CO₂]₂ was altered so that the support was modified with 100 ppm CaO. Ethylene conversion was 10.1% and EO selectivity was 79.9% at 224° C.

Example 10

The catalyst was synthesized and tested as described in Example 8, except the amount of Ca[CH₃CH(OH)CO₂]₂ was altered so that the support was modified with 50 ppm CaO. Ethylene conversion was 10.3% and EO selectivity was 81.3% at 223° C.

Comparative Example 1

The support rings (Norpro SA5552) were directly used without any modification. The synthesized and tested as described in Example 1. Ethylene conversion was 10.2% and EO selectivity was 82.7% at 226° C.

TABLE 3

| Example | CaO ppm | T ° C. | Ethylene Conv. % | EO Sel. % | EO Yield % |
|---|---|---|---|---|---|
| 8 | 1000 | 214 | 10.1 | 78.8 | 7.9 |
| 9 | 100 | 224 | 10.1 | 79.9 | 8.1 |
| 10 | 50 | 223 | 10.3 | 81.3 | 8.4 |
| Comparative 1 | 0 | 226 | 10.2 | 82.7 | 8.4 |

CaSiO₃: Source: CaCl₂+Na₂SiO₃, 550° C., 5 hrs

Example 11

36.0 g support rings (Norpro SA5552) was impregnated with 9.7 ml of an aqueous solution of 4.07 wt % CaCl₂ (CaCl₂.2H₂O, Aldrich 99.99%) in a round flask. The impregnated support with residual solution was rotary evaporated under vacuum for 10 minutes or till no residual solution is visible. During the rotary evaporation, the flask was exposed to atmosphere for 2-3 times to ensure uniform distribution of the solution throughout the support. The impregnated support was then dried at 120° C. for 10 hours. The same procedure was followed to impregnate 9.7 ml of an aqueous solution of 8.54 wt % Na₂SiO₃ (Na₂SiO₃.9H₂O, Aldrich 99.9%). After the second impregnation, it was dried and calcined in a muffle furnace in air at 120° C. for 10 hours, 550° C. for 5 hours, and 900° C. for 5 hours before cooled to ambient temperature. The catalyst precursor was washed with 2 liters DI water at 90° C. to remove sodium and chlorine, repeated one more time so that the total time of washing was about 60 hours, and dried at 120° C. for 10 hours. This will result in a support containing 1.03 wt % CaSiO₃ (equivalent to 5000 ppm CaO).

The catalyst was synthesized and tested as described in Example 1. Ethylene conversion was 9.6% and EO selectivity was 80.6% at 216° C.

Example 12

The catalyst was synthesized and tested as described in Example 11, except the amount of CaCl₂ was altered so that the support was modified with 2 wt % CaSiO₃ (equivalent to 10000 ppm CaO) as described in Example 11. Ethylene conversion was 10.6% and EO selectivity was 80.1% at 217° C.

Example 13

The catalyst was synthesized and tested as described in Example 11, except the amount of CaCl₂ was altered so that the support was modified with 2070 ppm CaSiO₃ (equivalent to 1000 ppm CaO) as described in Example 11. Ethylene conversion was 9.9% and EO selectivity was 81.8% at 212° C.

Example 14

The catalyst was synthesized and tested as described in Example 11, except the amount of CaCl₂ was altered so that the support was modified with 620 ppm CaSiO₃ (equivalent to 300 ppm CaO) as described in Example 11. Ethylene conversion was 9.6% and EO selectivity was 82.3% at 224° C.

Example 15

The catalyst was synthesized and tested as described in Example 11, except the amount of CaCl₂ was altered so that the support was modified with 200 ppm CaSiO₃ (equivalent to 100 ppm CaO) as described in Example 11. Ethylene conversion was 10.4% and EO selectivity was 80.1% at 233° C.

Example 16

The catalyst was synthesized and tested as described in Example 11, except the amount of CaCl₂ was altered so that the support was modified with 100 ppm CaSiO₃ (equivalent to 50 ppm CaO) as described in Example 11. Ethylene conversion was 10.1% and EO selectivity was 80.6% at 223° C.

Example 17

The catalyst was synthesized and tested as described in Example 11, except the amount of CaCl₂ was altered so that the support was modified with 40 ppm CaSiO₃ (equivalent to 20 ppm CaO) as described in Example 11. Ethylene conversion was 9.8% and EO selectivity was 85.1% at 224° C.

TABLE 4

| Example | CaO ppm | T ° C. | Ethylene Conv. % | EO Sel. % | EO Yield % |
|---|---|---|---|---|---|
| 11 | 50000 | 216 | 9.6 | 80.6 | 7.7 |
| 12 | 10000 | 217 | 10.6 | 80.1 | 8.5 |
| 13 | 1000 | 212 | 9.9 | 81.8 | 8.1 |
| 14 | 300 | 224 | 9.6 | 82.3 | 7.9 |
| 15 | 100 | 233 | 10.4 | 80.1 | 8.3 |
| 16 | 50 | 223 | 10.1 | 80.6 | 8.1 |
| 17 | 20 | 224 | 9.8 | 85.1 | 8.3 |

$Na_2SiO_3$: Source: $Na_2SiO_3$, 550° C., 5 hrs

Example 18

35.2 g support rings (Norpro SA5552) was impregnated with 9.5 ml of an aqueous solution of 0.92 wt % $Na_2SiO_3$ ($Na_2SiO_3.9H_2O$, Aldrich 99.9%) in a round flask. The impregnated support with residual solution was rotary evaporated under vacuum for 10 minutes or till no residual solution is visible. During the rotary evaporation, the flask was exposed to atmosphere for 2-3 times to ensure uniform distribution of the solution throughout the support. The impregnated support was then dried at 120° C. for 10 hours, and calcined at 550° C. for 5 hours in a muffle furnace in air. The catalyst precursor was washed with 2 liters DI water at 90° C. to remove sodium, repeated two more times so that the total time of washing was about 96 hours, and dried at 120° C. for 10 hours. This will result in a support containing 1239 ppm $SiO_2$.

The catalyst was synthesized and tested as described in Example 1. Ethylene conversion was 10.3% and EO selectivity was 80.0% at 210° C.

Example 19

The catalyst was synthesized and tested as described in Example 18, except the amount of $Na_2SiO_3$ was altered so that the support was modified with 50 ppm $SiO_2$. Ethylene conversion was 10.4% and EO selectivity was 81.8% at 217° C.

Example 20

The catalyst was synthesized and tested as described in Example 18, except the amount of $Na_2SiO_3$ was altered so that the support was modified with 10 ppm $SiO_2$. Ethylene conversion was 10.1% and EO selectivity was 82.7% at 224° C.

TABLE 5

| Example | SiO2 ppm | T ° C. | Ethylene Conv. % | EO Sel. % | EO Yield % |
|---|---|---|---|---|---|
| 18 | 1070 | 210 | 10.3 | 80.00 | 8.2 |
| 19 | 50 | 217 | 10.4 | 81.8 | 8.5 |
| 20 | 10 | 224 | 10.1 | 82.7 | 8.4 |

Comparative Examples $CaWO_4$: Source: $Ca(NO_3)_2+(NH_4)10W_{12}O_{41}.H_2O$, 550° C., 5 hrs Comparative Example 2

26.5 g support rings (Norpro SA5552) was impregnated with 7.2 ml of an aqueous solution of 1.82 wt % $Ca(NO_3)_2$ ($Ca(NO_3)_2.4H_2O$, Aldrich, 99.99%) in a round flask. The impregnated support with residual solution was rotary evaporated under vacuum for 10 minutes or till no residual solution is visible. During the rotary evaporation, the flask was exposed to atmosphere for 2-3 times to ensure uniform distribution of the solution throughout the support. The support was then dried at 120° C. for 10 hours. The same procedure was followed to impregnate 7.2 ml of an aqueous solution of 1.62 wt % $(NH_4)_{10}W_{12}O_{41}.7H_2O$ (Riede-de Haen). After the second impregnation, the support was dried and calcined in a muffle furnace in air at 120° C. for 10 hours, and 550° C. for 5 hours. This will result in a support containing 5185 ppm $CaWO_4$ (equivalent to 1000 ppm CaO).

The catalyst was synthesized and tested as described in Example 1. Ethylene conversion was 0.6% and EO selectivity was 50.9% at 250° C.

Comparative Example 3

The support was modified as described in Comparative Example 2, except with 2590 ppm $CaWO_4$ (equivalent to 500 ppm CaO). The catalyst was synthesized and tested as described in Example 1. Ethylene conversion was 0.7% and EO selectivity was 78.7% at 220° C.

Comparative Example 4

The support was modified as described in Comparative Example 2, except with 260 ppm $CaWO_4$ (equivalent to 50 ppm CaO). The catalyst was synthesized and tested as described in Example 1. Ethylene conversion was 9.9% and EO selectivity was 80.7% at 227° C.

TABLE 6

| Comparative Example | CaWO4 ppm | T ° C. | Ethylene Conv. % | EO Sel. % | EO Yield % |
|---|---|---|---|---|---|
| 2 | 5180 | 250 | 0.6 | 50.9 | 0.3 |
| 3 | 2590 | 220 | 0.7 | 78.7 | 0.6 |
| 4 | 260 | 227 | 9.9 | 80.7 | 8.0 |

$WO_3$: Source: $(NH_4)_{10}W_{12}O_{41}.H_2O$, 550° C., 5 hrs

Comparative Example 5

The support was modified as described in Comparative Example 2, except with 200 ppm $WO_3$. The catalyst was synthesized and tested as described in Example 1. Ethylene conversion was 2.0% and EO selectivity was 70.8% at 250° C.

Comparative Example 6

The support was modified as described in Comparative Example 2, except with 2088 ppm $WO_3$. The catalyst was synthesized and tested as described in Example 1. Ethylene conversion was 10.0% and EO selectivity was 69.8% at 250° C.

TABLE 7

| Comparative Example | WO3 ppm | T °C. | Ethylene Conv. % | EO Sel. % | EO Yield % |
|---|---|---|---|---|---|
| 5 | 200 | 250 | 2.0 | 70.8 | 1.4 |
| 6 | 2088 | 250 | 10.0 | 69.8 | 7.0 |

The Examples evaluate treatment of an alumina support with different weak base is compounds with a subsequent heat treatment/calcination. Comparative Example 1 has neither treatment with a weak base compound nor a heat treatment/calcination. Comparative Examples 2-6 evaluate treatment of an alumina support with different acid compounds with a subsequent heat treatment/calcination. The above data demonstrate that, while the EO conversion in both the Examples and Comparative Examples was targeted to 10%, the Comparative Examples did not attain the targeted EO conversion without increasing the reaction temperature, i.e., the reaction temperature of the Comparative Examples (220-250° C.) is generally higher than that of the Examples (212-227° C.). Even with the increased reaction temperature many of the Comparative Examples did not consistently even attain the targeted EO conversion. In addition, the EO yield for the Comparative Examples was consistently lower than that for the Examples. This data show that treatment of the support with a weak base compound followed by a heat treatment or calcination improves catalyst performance for ethylene epoxidation.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A catalyst for oxidation of an alkene to an alkene oxide comprising:

a) a support of alpha-alumina; and
b) a catalytically effective amount of silver
wherein the alpha-alumina support contains a weak base compound having a partial charge of from about −0.3 to about −0.95 and selected from oxides of Group 1A or Group 2A of the Periodic Table of Elements and
wherein the support contains an amount of the weak base compound in the range from 20 to 10,000 ppm at a depth of 1.5 to 40 angstroms.

2. The catalyst of claim 1 wherein the silver is at from about 2-50 percent by weight.

3. The catalyst of claim 2 wherein the silver is from about 5-30 percent by weight.

4. The catalyst of claim 3 wherein the silver is from about 8-15 percent by weight.

5. The catalyst of claim 1 further comprising promoters which are compounds of sodium, potassium, rubidium or cesium.

6. The catalyst of claim 5 wherein the promoter compounds are cesium hydroxide, cesium chloride or cesium nitrate.

7. The catalyst of claim 5 wherein the promoter compound is present in the amount of from about 20-5000 ppm.

8. The catalyst of claim 7 wherein the promoter compound is present in the amount of from about 50-2000 ppm.

9. The catalyst of claim 8 wherein the promoter compound is present in the amount from about 100-1000 ppm.

10. The catalyst of claim 1 wherein the weak base compound is calcium oxide (CaO).

11. The catalyst of claim 1 wherein the weak base compound contains additional elements selected from the group consisting of aluminum, silicon, phosphorus, gallium, germanium and arsenic.

12. The catalyst of claim 11 wherein the weak base compound is calcium silicate or sodium silicate.

13. The catalyst of claim 1 wherein the support contains an amount of the weak base compound in the range from 50 to 1000 ppm.

* * * * *